(12) United States Patent
Kim et al.

(10) Patent No.: US 9,035,260 B2
(45) Date of Patent: May 19, 2015

(54) RADIATION MEASURING SYSTEM BASED ON OPTIMAL MEASUREMENT GEOMETRY AND RADIATION MEASURING METHOD USING THE SAME

(71) Applicants: Hee Geun Kim, Daejeon (KR); Tae Young Kong, Daejeon (KR)

(72) Inventors: Hee Geun Kim, Daejeon (KR); Tae Young Kong, Daejeon (KR)

(73) Assignee: KOREA HYDRO & NUCLEAR POWER CO. LTD., Gyeongsanbuk-Do (KR)

( * ) Notice: Subject to any disclaimer, the term of this patent is extended or adjusted under 35 U.S.C. 154(b) by 171 days.

(21) Appl. No.: 13/735,462

(22) Filed: Jan. 7, 2013

(65) Prior Publication Data

US 2013/0190620 A1    Jul. 25, 2013

(30) Foreign Application Priority Data

Jan. 25, 2012    (KR) ........................ 10-2012-0007183

(51) Int. Cl.
*G01F 23/00*    (2006.01)
*A61B 6/00*    (2006.01)
*G01T 1/163*    (2006.01)

(52) U.S. Cl.
CPC ............... *A61B 6/4275* (2013.01); *A61B 6/50* (2013.01); *A61B 6/5217* (2013.01); *A61B 6/54* (2013.01); *G01T 1/163* (2013.01)

(58) Field of Classification Search
USPC ........................................ 250/358.1
See application file for complete search history.

(56) References Cited

U.S. PATENT DOCUMENTS

| 8,242,456 B1 * | 8/2012 | Hecht et al. ................. 250/393 |
| 2004/0037394 A1 * | 2/2004 | Kuroda et al. ............... 378/205 |
| 2011/0073761 A1 * | 3/2011 | Kong et al. ................. 250/336.1 |

FOREIGN PATENT DOCUMENTS

KR    2011-0033614 A    3/2011

* cited by examiner

*Primary Examiner* — David Porta
*Assistant Examiner* — Edwin Gunberg
(74) *Attorney, Agent, or Firm* — Leydig, Voit & Mayer, Ltd.

(57) ABSTRACT

A radiation measuring system includes a whole-body counter having upper and lower radiation detectors that are located in front of a measurement space, which has an inlet passage and is located in a housing, and that detects respective internal radiations of a measurement target and first and second internal radiations of a body region corresponding to one of a thyroid gland, a lung, a whole body, or a hypogastrium, and a processor controlling determination of an internal radioactive contamination location of the measurement target, based on a ratio of the first and second internal radiations, applying the optimal measurement mode corresponding to the ratio of the first and second internal radiations, and detecting the first and second internal radiations of a body region corresponding to the internal radioactive contamination location.

4 Claims, 5 Drawing Sheets

RADIATION MEASURING SYSTEM BASED ON OPTIMAL MEASUREMENT GEOMETRY AND RADIATION MEASURING METHOD USING THE SAME

TECHNICAL FIELD

The present invention relates to a whole-body counter and, more particularly, to a radiation measuring system in which radiation emitted from contaminated radioactive materials is measured using a detector in connection with internal radioactive contamination of the body in which a radiation worker may undergo during radiation work, and a radiation measuring method using the same.

BACKGROUND ART

Conventional internal radioactive contamination whole-body counters are configured so that two upper and lower radiation detectors are installed in front of a measurement space in the whole-body counter in order to measure internal radioactive contamination of a radiation worker. Thus, the upper and lower radiation detectors of the whole-body counter measure radiations emitted from the body of the worker contaminated with internal radiations, add the measured radiations, and calculate a value of measurement of the internal radiations. Particularly, when a radioactive material inhaled by the radiation worker is located in an upper portion of the body, the upper radiation detector of the whole-body counter measures relatively more radiations. However, when the inhaled radioactive material is located in a lower portion of the body, the lower radiation detector measures relatively more radiations.

Meanwhile, another type of whole-body counter used to determine the internal radioactive contamination of the radiation worker and to measure the contaminated radiations is equipped with one radiation detector installed in front of the measurement space. This whole-body counter measures the radiations emitted from the body of the measurement target while the radiation detector slowly moves from the top to the bottom, and calculates internal radiations using a value of measurement of the radiations. Since there is no radiation shielding wall in front of the measurement space, natural radiations or surrounding scattered radiations may be introduced into the radiation detector when the whole body is measured. Thus, the value of measurement of the radiations may have an error value. For this reason, the whole-body counter having the upper and lower radiation detectors in which the natural radiations are shielded is mainly used.

Typically, to monitor the internal radioactive contamination of the worker in radiation use facilities and atomic energy related facilities, radiation measurement is performed on all workers who have a possibility of inhaling radioactive materials during radiation work using an internal radioactive contamination whole-body counter. Meanwhile, the radioactive materials introduced into a human body are characterized in that they are uniformly distributed in a whole body or are concentrated and deposited in a specific organ such as a thyroid gland, a lung, or a hypogastrium. Thus, to increase precision of a radiation measurement value according to a deposition location of the radioactive materials when the internal radiations are measured and to correct the measurement value, the internal radioactive contamination whole-body counter is designed to be able to apply four measurement geometries for the whole body, the thyroid gland, the lung, and the hypogastrium to perform the measurement. However, since it is typically impossible to know accurately in which location of the human body the radioactive materials inhaled by the worker are deposited, the internal radiation measurement is performed using the whole-body measurement mode for calculating a highest or conservative radiation measurement value. The whole-body measurement mode of the internal radioactive contamination whole-body counter is adapted to calculate the highest measurement value on the assumption that the radioactive materials introduced into the human body are uniformly distributed in the whole body, and to calculate a value that is 2.5 to 1.5 times higher than a value obtained by measuring the internal radiations using the other measurement mode such as the thyroid gland, lung, or hypogastrium measurement mode even when the worker inhales the radioactive materials of the same concentration. This whole-body measurement mode has a problem in that a dose of radiation exposure of the radiation worker is incorrectly estimated in a very conservative way, because it not only fails to properly indicate the internal radioactive contamination location of the radiation worker but also calculates the internal radiation measurement value as a high value. Meanwhile, the dose of radiation exposure of the radiation worker is regulated so as not to exceed an annual dose limit. Thus, by conservatively calculating the internal radiation measurement value as a high value, wrong information about the dose of radiation exposure is provided to the radiation worker, which may increase a risk of industrial accidents such as occupational diseases due to the outbreak of radiation excessive cancer resulting from excessive exposure in the future.

A whole-body counter for discrimination between internal and external radioactive contamination is disclosed in Korean Unexamined Patent Publication No. 10-2011-0033614, in which the precision of radioactive contamination measurement is improved by additionally installing a plurality of radiation counters on conventional internal radioactive contamination measuring equipment to discriminate between internal and external radioactive contamination of a worker. However, Korean Unexamined Patent Publication No. 10-2011-0033614 does not provide a function of determining in which location of a human body radioactive materials inhaled by the radiation worker are deposited, and thus has a disadvantage in that a radiation measurement value is not accurate because internal radiations are measured using only a whole-body measurement mode regardless of the location contaminated with the radioactive materials, and thus a dose of radiation exposure of the worker is conservatively (excessively) estimated.

Technical Problem

Accordingly, the present invention has been made keeping in mind the above problems occurring in the related art, and an object of the present invention is to provide a whole-body counter providing an optimized measurement mode capable of determining a radioactive contamination location in a human body using a measurement ratio of upper and lower radiation detectors and of increasing precision of radiation measurement, and a radiation measuring method using the same.

Technical Solution

According to an aspect of the present invention, a radiation measuring system based on an optimal measurement mode includes: a whole-body counter having upper and lower radiation detectors that are installed in front of a measurement space, which has an inlet passage and is formed in a housing, and that detect respective internal radiations of a measurement target and then first and second internal radiations of a body region corresponding to one of a thyroid gland, a lung, a whole body, and a hypogastrium; and a processor controlling to determine an internal radioactive contamination location of the measurement target based on a ratio of the first and second internal radiations, to apply the optimal measurement mode corresponding to the ratio of the first and second internal radiations, and to additionally detect the first and second internal radiations of a body region corresponding to the determined internal radioactive contamination location.

According to an aspect of the present invention, a radiation measuring method based on an optimal measurement mode includes: detecting first and second internal radiations of a measurement target using respective upper and lower radiation detectors installed in front of a measurement space that has an inlet passage and is formed in a housing; calculating a ratio of the first internal radiation of the measurement target which is detected by the upper radiation detector and the second internal radiation of the measurement target which is detected by the lower radiation detector; determining whether the ratio of the first and second internal radiations belongs to a first range, a second range, a third range, or a fourth range; applying one of a thyroid gland measurement mode, a lung measurement mode, a whole-body measurement mode, and a hypogastrium measurement mode according to a result of the determination to detect the first and second internal radiations of a body region corresponding to one of a thyroid gland, a lung, a whole body, and a hypogastrium; and adding and outputting the detected first and second internal radiations of the corresponding body region.

Advantageous Effects

As described above, the internal radioactive contamination whole-body counter of the present invention determines an internal radioactive contamination location on the basis of a measurement ratio calculated by the upper and lower radiation detectors in connection with the internal radioactive contamination of a worker which may take place during radiation work, and applies an optimal measurement mode based on the contamination location to provide an internal radiation measurement value.

The conventional internal radioactive contamination whole-body counter does not provide a function of determining in which location of a human body radioactive materials inhaled by a radiation worker are deposited, and thus has a disadvantage in that internal radiation is measured using only a whole-body measurement mode regardless of the location contaminated with the radioactive materials, and in that a dose of radiation exposure of the worker is conservatively estimated. However, the whole-body counter of the present invention determines the internal radioactive contamination location of the radiation worker and thus provides an optimal measurement mode based on the contamination location, thereby improving precision of the internal radiation measurement.

Korea Hydro & Nuclear Power Co. Ltd. allocated expenses of about 35 billion wons from 1991 to 2000 in observing the radiological protection recommendations of the International Commission on Radiological Protection and reducing the radiation exposure of radiation workers of nuclear power plants, and expenses of about 190 billion wons from 2001 to 2010 in reducing the radiation exposure. In this way, reduction of the radiation exposure of radiation workers is closely related to the operation of the nuclear power plant. The radiation measurement performed conservatively at present is more accurately performed, and thereby it is expected that potential operation expenses of the nuclear power plant can be greatly reduced.

MODE FOR INVENTION

Hereinafter, the operational principle of the present invention will be described in detail below with reference to the accompanying drawings. If, in the following description of the present invention, detailed descriptions of well-known functions or constructions may unnecessarily make the gist of the present invention obscure, the detailed descriptions will be omitted. The following terms are defined in consideration of functions in the present invention, and the meanings thereof may vary according to the custom or intention of a user or an operator or according to usual practice. Therefore, the definitions of the terms must be interpreted based on the entire content of the present specification.

Figure 1:
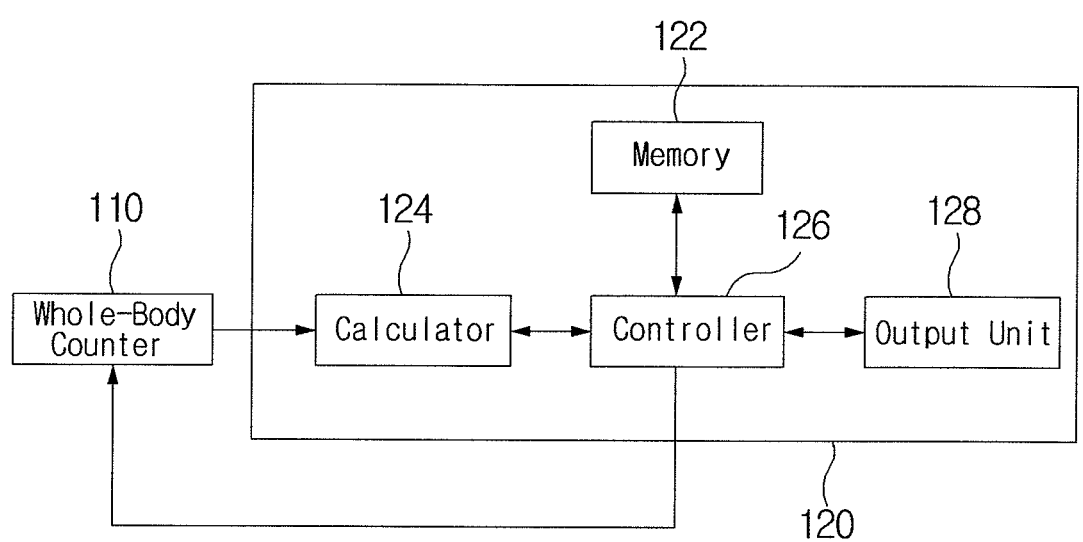
FIG. 1 is a block diagram showing a configuration of a radiation measuring system based on an optimal measurement mode in accordance with an embodiment of the present invention.

FIG. 1 is a block diagram showing a configuration of a radiation measuring system based on an optimal measurement mode in accordance with an embodiment of the present invention.

The radiation measuring system based on an optimal measurement mode in accordance with the embodiment of the present invention includes a whole-body counter 110 and a processor 120.

The whole-body counter 110 includes upper and lower radiation detectors that are installed in front of a measurement space 230 or 330, which has an inlet passage and is formed in a housing, and that detect respective internal radiations of a measurement target and then first and second internal radiations of a body region corresponding to one of a thyroid gland, a lung, a whole body, and a hypogastrium.

Figure 2:
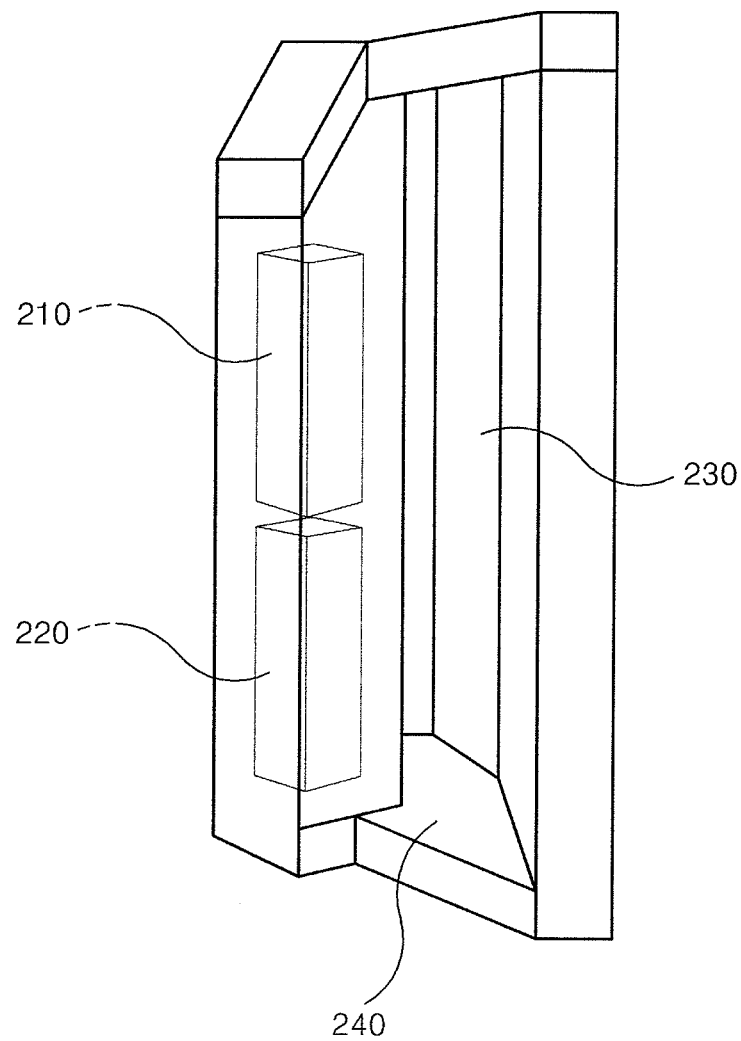
FIG. 2 is a schematic perspective view showing an example of the whole-body counter shown in FIG. 1.
Figure 3:
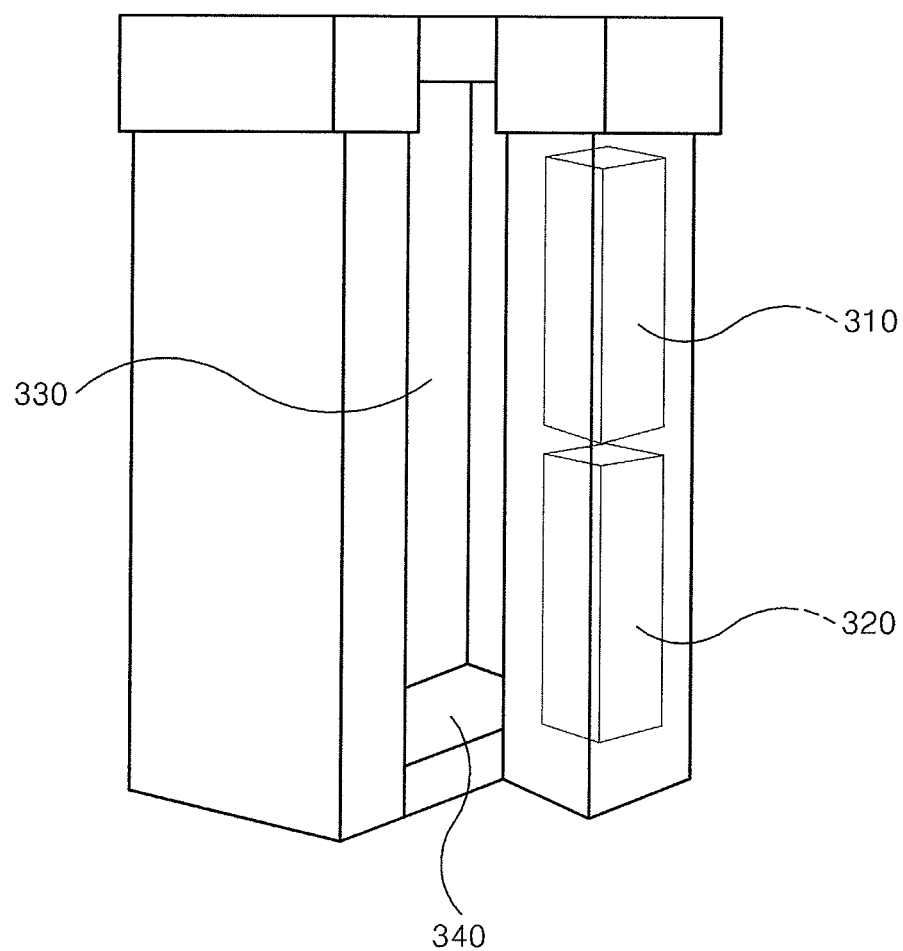
FIG. 3 is a schematic perspective view showing another example of the whole-body counter shown in FIG. 1.

FIG. 2 is a schematic perspective view showing an example of the whole-body counter shown in FIG. 1. FIG. 3 is a schematic perspective view showing another example of the whole-body counter shown in FIG. 1. Referring to FIGS. 2 and 3, the whole-body counter is formed in a vertical linear geometry, has a measurement space 230 or 330 formed in a hexagonal or rectangular prism housing, has a passage in the front thereof so as to enable a radiation worker to enter the measurement space, and is equipped with upper radiation detectors 210 and 310 and lower radiation detectors 220 and 320 in front of the measurement space 230 or 330. Further, the measurement space of the whole-body counter is sealed by a steel plate so as to shield natural radiation around the radiation detectors and the radiation worker that is the measurement target. As such, no radiation is introduced from the outside toward the radiation detectors, and scattered radiation is processed as natural radiation. When internal radiation of the radiation worker is measured, the radiation emitted from the radiation worker interacts with media of the upper and lower radiation detectors to generate electric signals. An electronic circuit installed in the whole-body counter adds the signals generated from the upper and lower radiation detectors to calculate a value of radiation measurement.

The processor 120 controls to determine an internal radioactive contamination location of the measurement target based on a ratio of the first and second internal radiations detected by the whole-body counter 110, to apply an optimal measurement mode corresponding to the ratio of the first and second internal radiations, and to additionally detect the first and second internal radiations of a body region corresponding to the determined internal radioactive contamination location.

Referring to FIG. 1 again, the processor 120 includes a memory 122, a calculator 124, a controller 126, and an output unit 128.

The memory 122 stores a lookup table in which first, second, third, and fourth ranges, to which the ratio of the internal radiations of the measurement target to be detected by the upper and lower radiation detectors 210 and 220 belongs, correspond to a thyroid gland measurement mode, a lung measurement mode, a whole-body measurement mode, and a hypogastrium measurement mode, respectively. The first, second, third, and fourth ranges preferably have a ratio of a value between 80 and 100 to a value between 0 and 20, a ratio of a value between 65 and 80 to a value between 20 and 35, a ratio of a value between 40 and 65 to a value between 35 and 60, and a ratio of a value between 0 and 40 to a value between 60 and 100, respectively.

The calculator 124 calculates a ratio of the first internal radiation of the measurement target which is detected by the upper radiation detector 210 and the second internal radiation of the measurement target which is detected by the lower radiation detector 220, adds the re-detected first and second internal radiations of the corresponding body region, and obtains an added value.

The controller 126 determines whether the ratio of the first and second internal radiations belongs to the first, second, third, or fourth range with reference to the lookup table stored in the memory 122, and determines a human body internal radioactive contamination location according to a result of the determination. The controller 126 controls the upper and lower radiation detectors to apply one of the thyroid gland measurement mode, the lung measurement mode, the whole-body measurement mode, and the hypogastrium measurement mode according to the result of the determination, and to additionally detect the first and second internal radiations of the body region corresponding to one of the thyroid gland, the lung, the whole body, and the hypogastrium.

In connection with the whole-body counter of the radiation measuring system based on an optimal measurement mode in accordance with the present invention, to check how conservatively a value of internal radiation measurement is calculated when only the whole-body measurement mode is used for the internal radiation measurement without considering a deposition location of the radioactive material, the deposition location of the radioactive material and the internal radiation based on the whole-body counter measurement mode were measured using a phantom and a liquid gamma mixed source for calibration of the whole-body counter. The results of performing the radiation measurement experiment on each measurement mode of the internal radioactive contamination whole-body counter are collectively shown in Table 1. As shown in Table 1, it can be seen that the value of radiation measurement performed on the thyroid gland, the lung, the whole body, and the hypogastrium that are the deposition regions of the internal radioactive material of the human body using the whole-body measurement mode is highest. This shows that, when only the whole-body measurement mode is used for the internal radiation measurement without considering the deposition location of the internal radioactive material of the human body, a quantity of radiation of the corresponding radioactive material is conservatively overestimated. In contrast, when the measurement mode is incorrectly selected (e.g., when another measurement mode is used even though radioactive nuclides are distributed in the whole body), this shows a result that the quantity of radiation of the corresponding radioactive material is subjected to conservative estimation and is underestimated. Thus, when an optimized measurement mode according to a human body internal deposition location of the radioactive material should be selected for whole-body measurement, the quantity of radiation maintained in the body of the radiation worker can be accurately measured.

TABLE 1

| Radioactive Material Deposition Location | Measurement Geometry | Phantom for Calibration of Whole-Body Counter Radioactivity (kBq) | |
|---|---|---|---|
| | | Co-60 | Cs-137 |
| Thyroid Gland | Whole Body | 12.5 | 10.0 |
| | Thyroid Gland | 5.6 | 3.9 |
| | Lung | 9.6 | 7.5 |
| | Hypogastrium | 9.5 | 8.2 |
| Lung | Whole Body | 7.3 | 5.5 |
| | Thyroid Gland | 3.3 | 2.1 |
| | Lung | 5.7 | 3.7 |
| | Hypogastrium | 5.8 | 4.1 |
| Whole Body | Whole Body | 5.8 | 4.0 |
| | Thyroid Gland | 2.6 | 1.6 |
| | Lung | 4.1 | 2.9 |
| | Hypogastrium | 4.4 | 3.0 |
| Hypogastrium | Whole Body | 7.2 | 5.3 |
| | Thyroid Gland | 3.3 | 1.9 |
| | Lung | 5.8 | 3.7 |
| | Hypogastrium | 5.5 | 3.8 |
| True Value | | 5.6 ± 0.1 | 3.7 ± 0.1 |

The output unit 128 outputs the added value of the detected first and second internal radiations of the corresponding body region from the calculator 124.

Figure 4:
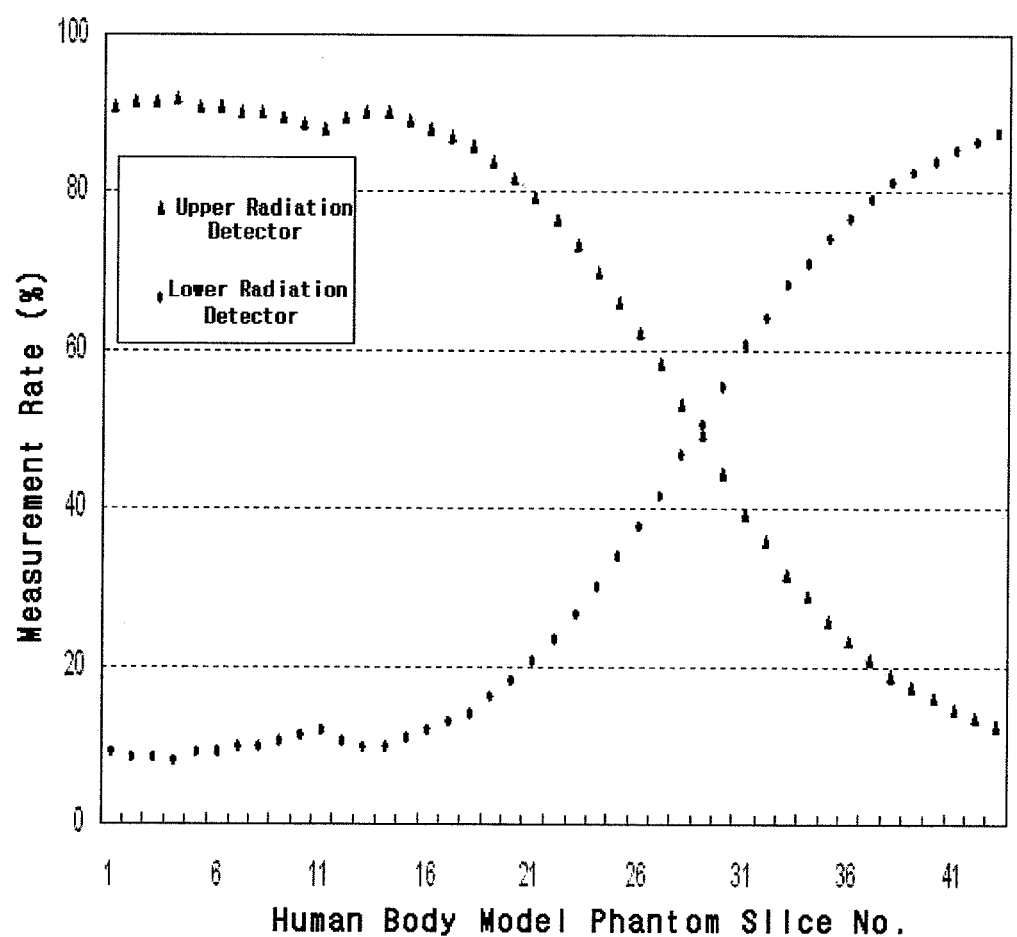
FIG. 4 is a graph showing a measurement ratio of upper and lower radiation detectors of the internal radioactive contamination whole-body counter according to a radiation source location in a human body model, i.e. a phantom, in accordance with an embodiment of the present invention.

FIG. 4 is a graph showing a measurement ratio of the upper and lower radiation detectors of the internal radioactive contamination whole-body counter according to a radiation source location in a human body model, i.e. a phantom, in accordance with an embodiment of the present invention.

Figure 5:
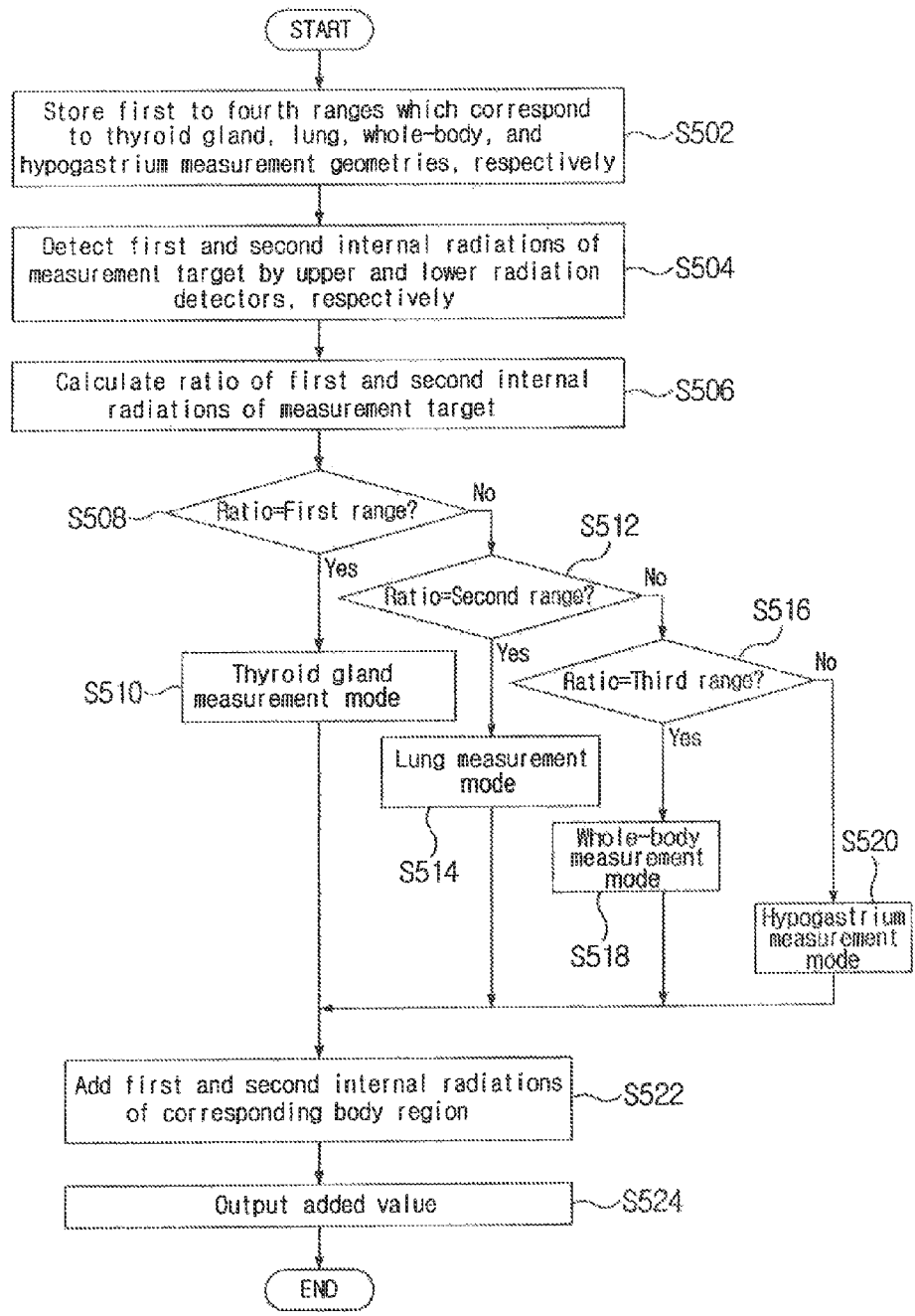
FIG. 5 is a flow chart for describing a radiation measuring method based on an optimal measurement mode in accordance with an embodiment of the present invention.

Hereinafter, a radiation measuring method based on an optimal measurement mode in accordance with an embodiment of the present invention will be described with reference to FIG. 5. FIG. 5 is a flow chart for describing a radiation measuring method based on an optimal measurement mode in accordance with an embodiment of the present invention.

The controller 126 stores a first range (a ratio of a value between 80 and 100 to a value between 0 and 20), a second range (a ratio of a value between 65 and 80 to a value between 20 and 35), a third range (a ratio of a value between 40 and 65 to a value between 35 and 60), and a fourth range (a ratio of a value between 0 and 40 to a value between 60 and 100), to which a ratio of internal radiations of a measurement target to be detected by the upper and lower radiation detectors belongs, and which correspond to a thyroid gland measurement mode, a lung measurement mode, a whole-body measurement mode, and a hypogastrium measurement mode respectively, in the memory 122 (S502).

The upper and lower radiation detectors 210 and 220 installed in front of the measurement space 100 and 200, which has an inlet passage and is formed in a housing, detect the internal radiations of the measurement target, respectively (S504).

The calculator 124 calculates the ratio of the first internal radiation of the measurement target which is detected by the upper radiation detector 210 and the second internal radiation of the measurement target which is detected by the lower radiation detector 220 (S506).

When the internal radiation of the radiation worker is measured using the internal radioactive contamination whole-body counter of the present invention, it is impossible to know in which locations the radioactive materials introduced into a human body are deposited. For this reason, on the assumption that the radioactive materials are uniformly distributed on the whole body of the worker, the whole-body measurement mode is applied to measure the internal radiations, and the radiation measurement ratios measured by the upper and lower radiation detectors are determined. When the ratios of the upper and lower radiation detectors are 1) a ratio of a value between 80 and 100 to a value between 0 and 20, 2) a ratio of a value between 65 and 80 to a value between 20 and 35, 3) a ratio of a value between 40 and 65 to a value between 35 and 60, and 4) a ratio of a value between 0 and 40 to a value between 60 and 100, a thyroid gland measurement mode, a lung measurement mode, a whole-body measurement mode, and a hypogastrium measurement mode are respectively applied to measure the internal radiations again. The values of measurement of the upper and lower radiation detectors are added to calculate a final internal radiation measurement value.

Particularly, the present invention is designed to determine the measurement ratios of the upper and lower radiation detectors of the whole-body counter when the internal radiations are measured in order to increase precision of the internal radiation measurement value, to reasonably find the internal radioactive contamination location of the radiation worker, to apply the optimized measurement mode corresponding to the contamination location to measure the internal radiations again, and to output the measurement values. Here, depending on in which of the thyroid gland, the lung, the whole-body, and the hypogastrium the radioactive materials introduced into the radiation worker are deposited, the measurement ratios of the upper and lower radiation detectors of the whole-body counter vary. According to the four measurement ratio ranges shown in FIG. 5, the optimal measurement mode coordinated with the corresponding contamination location is selected, and is applied to measure the internal radiations.

In connection with a function of the optimized measurement mode provided in the internal radiation measuring system of the present invention, to check the deposition location of the radioactive material introduced into the radiation worker and to set the measurement ratios of the upper and lower radiation detectors of the whole-body counter, an experiment for discriminating between internal and external radioactive contaminations using the phantom or the human body model patterned on a person and the standard radiation source (point source) was performed. The phantom used in this experiment met the requirements of the reference male (height: 173 cm, weight: 73 kg, etc.) suggested by the International Commission on Radiological Protection. Cobalt-60 and cesium-137 that are point sources were inserted into all slices of the phantom, and the internal radiations were measured using the whole-body counter. As shown in FIG. 4, the point sources were sequentially inserted between a first slice corresponding to the head of the phantom and a forty-third slice as a lowest slice corresponding to the hypogastrium, and the measurement rates of the upper and lower radiation detectors when the internal radiations were measured are shown. As shown, at a location of the head of the phantom, the measurement rate of the upper radiation detector was about 90%, and the measurement rate of the lower radiation detector was about 10%. It is shown that the former is remarkably higher than the latter, and that, as the inserted location of the point sources moves toward a lower portion of the phantom, the measurement rate of the lower radiation detector is increased, whereas the measurement rate of the upper radiation detector is reduced. That is, the ratio of the measurement rates of the upper and lower radiation detectors of the whole-body counter is shown as 85:15 at a location of the thyroid gland in the human body, as 75:25 at a location of the lung, as 60:40 at a location of the whole body, and as 35:65 at a location of the hypogastrium. The results of the experiment performed on the measurement rates of the upper and lower radiation detectors of the internal radioactive contamination whole-body counter at principal deposition locations of the radioactive materials in the human body are collectively shown in Table 2.

TABLE 2

| Measurement rate/<br>Principal Deposition<br>Location in Body | Rate of Upper Radiation<br>Detector (%) | Rate of Lower Radiation<br>Detector (%) |
|---|---|---|
| Thyroid Gland | 85 | 15 |
| Lung | 75 | 25 |
| Whole Body | 60 | 40 |
| Hypogastrium | 35 | 65 |

The controller 126 determines whether the ratio of the first and second internal radiations belongs to the stored first range (ratio of the value between 80 and 100 to the value between 0 and 20) (S508).

When the result of the determination of step S508 shows that the ratio of the first and second internal radiations belongs to the first range (ratio of the value between 80 and 100 to the value between 0 and 20), the upper and lower radiation detectors 210 and 220 apply the thyroid gland measurement mode to detect the first and second internal radiations of the thyroid gland region under control of the controller 126 (S510).

When the result of the determination of step S508 shows that the ratio of the first and second internal radiations does not belong to the stored first range (ratio of the value between 80 and 100 to the value between 0 and 20), the controller 126 determines whether the ratio of the first and second internal radiations belongs to the second range (ratio of the value between 65 and 80 to the value between 20 and 35) (S512).

When the result of the determination of step S512 shows that the ratio of the first and second internal radiations belongs to the stored second range (ratio of the value between 65 and 80), the upper and lower radiation detectors 210 and 220 apply the lung measurement mode to detect the first and second internal radiations of the lung region under control of the controller 126 (S514).

When the result of the determination of step S512 shows that the ratio of the first and second internal radiations does not belong to the second range (ratio of the value between 65 and 80 to the value between 20 and 35), the controller 126 determines whether the ratio of the first and second internal radiations belongs to the third range (ratio of the value between 40 and 65 to the value between 35 and 60) (S516).

When the result of the determination of step S516 shows that the ratio of the first and second internal radiations belongs to the third range (ratio of the value between 40 and 65 to the value between 35 and 60), the upper and lower radiation detectors 210 and 220 apply the whole-body measurement mode to detect the first and second internal radiations of the whole body under control of the controller 126 (S518). In contrast, when the result of the determination of step S516 shows that the ratio of the first and second internal radiations does not belong to the third range (ratio of the value between 40 and 65 to the value between 35 and 60), the controller 126 determines that the ratio of the first and second internal radiations belongs to the fourth range (ratio of the value between 0 and 40 to the value between 60 and 100), and the upper and lower radiation detectors 210 and 220 apply the hypogastrium measurement mode to detect the first and second internal radiations of the hypogastrium region under control of the controller 126 (S520).

The calculator 124 adds the detected first and second internal radiations of the corresponding body region to obtain an added value (S522), and the output unit 128 outputs the added value.

While the exemplary embodiment of the present invention has been described, it will be appreciated to those skilled in the art that various modifications, additions, and substitutions are possible without departing from the scope and spirit of the present invention as disclosed in the accompanying claims.

| Description of Numerals | |
|---|---|
| 110: whole-body counter | 120: processor |
| 122: memory | 124: calculator |
| 126: controller | 128: output unit |
| 210, 310: upper radiation detector | |
| 220, 320: lower radiation detector | |
| 230, 330: measurement space | 240, 340: inlet passage |

The invention claimed is:

1. A radiation measuring system comprising:
a whole-body counter having upper and lower radiation detectors that are installed in front of a measurement space, wherein
the measurement space has an inlet passage and is located in a housing, and
the counter detects respective internal radiations of a measurement target and first and second internal radiations of a human body region corresponding to one of a thyroid gland, a lung, a whole body, and a hypogastrium; and
a processor including:
a calculator calculating a ratio of the first internal radiation of the measurement target, which is detected by the upper radiation detector, to the second internal radiation of the measurement target, which is detected by the lower radiation detector, and adding the detected first and second internal radiations of the corresponding body region to produce an added value;
a controller
determining whether the ratio of the first and second internal radiations is within a first range of between 80 and 100 to between 0 and 20, a second range of between 65 and 80 to between 20 and 35, a third range of between 40 and 65 to between 35 and 60, or a fourth range of between 0 and 40 to between 60 and 100, by referencing lookup tables,
determining an internal radioactive contamination location of the human body according to the ratio, controlling the upper and lower radiation detectors to apply a thyroid gland measurement mode if the ratio is within the first range, to apply a lung measurement mode if the ratio is within the second range, to apply a whole-body measurement mode if the ratio is within the third range, or to apply a hypogastrium measurement mode if the ratio is within the fourth range, and
detecting the first and second internal radiations of the body region corresponding to one of the thyroid gland, the lung, the whole body, and the hypogastrium; and
an output unit outputting the added value of the detected first and second internal radiations of the corresponding body region from the calculator.

2. The radiation measuring system according to claim 1, wherein the processor includes:
a memory storing the lookup tables in which the first, second, third, and fourth ranges, to which the ratio of the internal radiations of the measurement target to be detected by the upper and lower radiation detectors pertains, correspond to the thyroid gland measurement mode, the lung measurement mode, the whole-body measurement mode, and the hypogastrium measurement mode, respectively.

3. A radiation measuring method comprising:
detecting respective first and second internal radiations of a measurement target using upper and lower radiation detectors located in front of a measurement space that has an inlet passage and is located in a housing;
calculating a ratio of the first internal radiation of the measurement target, which is detected by the upper radiation detector, to the second internal radiation of the measurement target, which is detected by the lower radiation detector;
determining whether the ratio of the first and second internal radiations is within a first range of between 80 and 100 to between 0 and 20, a second range of between 65 and 80 to between 20 and 35, a third range of between 40 and 65 to between 35 and 60, or a fourth range of between 0 and 40 to between 60 and 100, all of which are stored;
applying a thyroid gland measurement mode if the ratio is within the first range, a lung measurement mode if the ratio is within the second range, a whole-body measurement mode if the ratio is within the third range, or a hypogastrium measurement mode if the ratio is within the fourth range, according to the detections of the first and second internal radiations of a body region corresponding to one of a thyroid gland, a lung, a whole body, and a hypogastrium; and
adding and outputting the detected first and second internal radiations of the corresponding body region.

4. The radiation measuring method according to claim 3, further comprising storing the first, second, third, and fourth ranges which correspond to the thyroid gland, lung, whole-body, and hypogastrium measurement modes, respectively, and to which the ratio of the internal radiations of the measurement target to be detected by the upper and lower radiation detectors pertains.

* * * * *